United States Patent
Harris et al.

(10) Patent No.: US 10,317,382 B2
(45) Date of Patent: Jun. 11, 2019

(54) GAS SENSOR PACKAGING INCLUDING STRUCTURE TO MAINTAIN DEVICES IN A STATE OF READINESS

(71) Applicant: Life Safety Distribution AG, Hegnau (CH)

(72) Inventors: Stuart Alistair Harris, Bournemouth (GB); Richard James Peacock, Poole (GB); Graeme Ramsay Mitchell, Poole (GB)

(73) Assignee: Life Safety Distribution AG, Hegnau (CH)

(*) Notice: Subject to any disclaimer, the term of this patent is extended or adjusted under 35 U.S.C. 154(b) by 591 days.

(21) Appl. No.: 14/564,804

(22) Filed: Dec. 9, 2014

(65) Prior Publication Data

US 2015/0241380 A1  Aug. 27, 2015

Related U.S. Application Data

(60) Provisional application No. 61/945,448, filed on Feb. 27, 2014.

(51) Int. Cl.
*G01N 33/00* (2006.01)
*G01N 35/00* (2006.01)
*G01N 33/487* (2006.01)

(52) U.S. Cl.
CPC ..... *G01N 33/0031* (2013.01); *G01N 33/4875* (2013.01); *G01N 33/48778* (2013.01); *G01N 2035/00297* (2013.01); *Y10T 29/49002* (2015.01)

(58) Field of Classification Search
None
See application file for complete search history.

(56) References Cited

U.S. PATENT DOCUMENTS

| | | | | |
|---|---|---|---|---|
| 4,421,233 A * | 12/1983 | Burnett | ............... | H01L 23/60 206/503 |
| 4,941,961 A * | 7/1990 | Noguchi | ............... | C25D 17/10 204/280 |
| 5,421,189 A * | 6/1995 | Dussault | ............... | G01N 33/007 439/188 |
| 5,662,833 A * | 9/1997 | Laakso | ............... | C08L 61/06 252/500 |
| 6,109,445 A * | 8/2000 | Beyer | ............... | H05K 13/0084 206/561 |
| 6,447,659 B1 * | 9/2002 | Peng | ............... | G01N 27/4045 204/402 |
| 2010/0310343 A1 * | 12/2010 | Mayer | ............... | G01D 18/00 414/222.07 |
| 2011/0253436 A1 * | 10/2011 | Hasegawa | ............... | H01G 11/74 174/259 |

* cited by examiner

*Primary Examiner* — Tamir Ayad
(74) *Attorney, Agent, or Firm* — Wick Phillips Gould & Martin, LLP

(57) ABSTRACT

Packaging for electronic components includes provisions to short selected electrodes of the components together. A plastic base portion with a plurality of component receiving cavities carries a flexible, carbonized shorting element which extends between cavities. The cavities include a recess which is adjacent to the shorting element. Components can be inserted into respective cavities, and some of the electrodes will contact the shorting element. Other electrodes will extend into the recess and not be shorted.

20 Claims, 2 Drawing Sheets

The foam is sized and orientated to allow selective shorting of the required pins. For example, in a 3 electrode sensor, it is undesirable to short all 3 electrode pins together, only the sensing and reference pins need to be shorted Section A-A

GAS SENSOR PACKAGING INCLUDING STRUCTURE TO MAINTAIN DEVICES IN A STATE OF READINESS

CROSS-REFERENCE TO RELATED APPLICATION

This application claims the benefit of the filing date of U.S. Provisional Application Ser. No. 61/945,448 filed Feb. 27, 2014, entitled, "Electrochemical Gas Sensor Packaging Including Means To Maintain Devices In A State Of Readiness". The '448 application is hereby incorporated herein by reference.

FIELD

The application pertains to structures which maintain gas sensors in a state of readiness for use. More particularly, the application pertains to packaging structures wherein gas sensor electrodes can be shorted together to minimize delays due to start-up or stabilization periods.

BACKGROUND

In gas detection instruments employing an electrochemical gas sensor, a potentiostatic drive circuit is normally used to hold the sensor electrodes at the required potentials. These potentials may be equal or there may be a bias between them to drive the required electrochemical behaviour.

The current generated by a sensor between the sensing and counter electrodes (or between one of these electrodes and an additional electrode) is amplified by additional circuitry. If the sensor is provided with a diffusion limiting gas access barrier and the electrode activity is adequate to consume all of the target gas entering the cell, then the current generated is proportional to the concentration of target gas in the environment.

If, prior to installation in an instrument, the relevant electrodes of a gas sensor have not been maintained at the required relative potentials, for example (they have been allowed to drift to their open circuit potentials), there will be a significant delay in the sensor achieving its optimum operating condition. This could be due to chemical species forming on the electrode or in the electrolyte which would be consumed or reacted under normal operating conditions. For example, the sensor may exhibit an erroneous, high baseline reading indicating the presence of gas when in fact this output is merely a reflection of internal cell processes.

Such effects gradually decline with continued operation, but there can be a significant delay before the sensor is capable of performing to specification. This is termed a start-up or stabilization period. Such periods can be many hours in extreme cases, depending on the design of the sensor, the performance requirements and the period for which the electrodes have been allowed to drift.

For manufacturers who build and calibrate instruments (which may contain several different electrochemical sensors), such start-up delays can be a significant problem. They can lengthen the cycle time of the manufacturing process which in turn requires the instrument manufacturer to hold additional inventory and hence increase costs.

Sensors which normally operate under bias are usually shipped on a pcb provided with a potentiostat and circuit capable of maintaining the required potentials for a limited period (compatible with the interval between sensor manufacture and instrument integration). The cost of such boards is not negligible and they are usually recycled back to the sensor manufacturer. This is time consuming and undesirable, but still preferable to dealing with long start-up times. For the majority of sensors which operate at zero bias, such complexity is not required, and creating a shorting connection between the relevant electrodes is adequate to maintain the sensor in a state of readiness.

The prior art discloses attaching a spring (or similar) across sensor contact pins to create an electrical short. This is additional labor task which is detrimental to the productivity of sensor manufacture, and an equal labor task is necessary for the instrument manufacturer to remove the spring before installation. Many instrument manufacturers opt to not install a spring. The reduced labor cost is more valuable than a cycle time associated with waiting for the drive circuit to stabilize the electrodes.

Preferably shorting links will only be applied between the required electrodes. Otherwise there is a risk of maintaining an electrode at an undesirable potential which can itself be a source of startup delay. For example, it may be undesirable to connect the counter electrode to the shorted sensing electrode-reference electrode pair, as in many cases it has a different Open Circuit Voltage and would therefore disturb the natural equilibrium of the reference.

Thus, an approach which unselectively shorts all sensor pins is unlikely to be appropriate. This is one reason why simple foam pads of the type used to protect semiconductor components from electrostatic discharge are not an adequate solution to the problem, even for individually packaged sensors. Similarly, approaches where a metal foil-covered compliant pad is used to short all the pins has significant shortcomings for sensor users, even if the relatively small annular contact areas of the foils around the pins were felt to be adequate and reliable. An ESD bag would suffer from similar shortcomings.

For containers holding multiple sensors, the above noted problems are greater.

Other shortcomings are (a) that the contacts between the sensor pins are not robustly and continuously maintained and can depend on orientation; and (b) the resistivity of the materials used is not well matched to the requirements of the electrochemical processes. For example, many ESD foams exhibit resistances of the order of 100K ohms between sensor pins. ESD bags have too high a resistance and offer insufficient contact area with the pins.

Electrochemical toxic gas sensors are packaged in a number of configurations which include (but are not limited to) multiple sensors packaged in trays, and individual sensors packaged in pots. Following the end of the manufacturing process, after exposing the sensors to a target gas to ensure sensor performance to a respective specification, the sensors are placed in storage locations or packaging trays.

Using prior art methods, additional handling of the sensors is necessary to apply the shorting spring, or similar structure, with the possibility of double handling if sensors are stored in an un-shorted state, with springs added prior to shipping.

DETAILED DESCRIPTION

Figure 1:
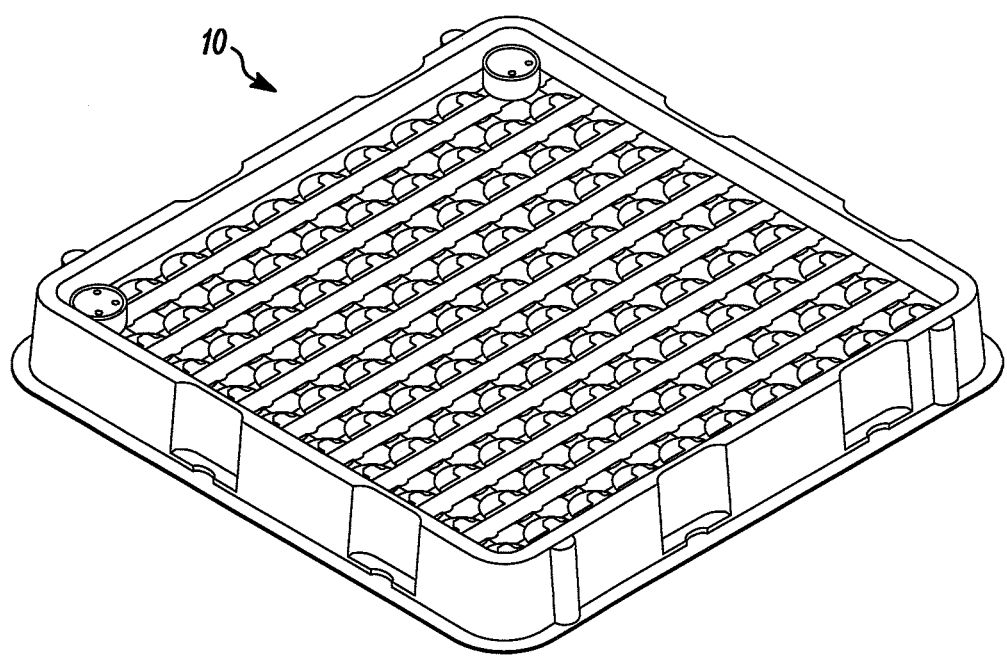
FIG. 1 illustrates a block diagram of a packaging system in accordance herewith.

While disclosed embodiments can take many different forms, specific embodiments thereof are shown in the drawings and will be described herein in detail with the understanding that the present disclosure is to be considered as an exemplification of the principles thereof as well as the best mode of practicing same, and is not intended to limit the application or claims to the specific embodiment illustrated.

In one aspect, in embodiments hereof a shorting medium is integrated into the packaging or storage container. The respective sensor is immediately shorted once placed in the storage container. By using a purposefully shaped conductive material a short can be created only between the required sensor contacts. Those contacts which do not require shorting are isolated from the shorted contacts.

By using a material which is conductive and has good elastic properties, contact resistance between the conductive material and the sensor contacts can be maintained prior to use by instrument manufacturers. The instrument manufacturer could then remove the sensor from the packaging without removing the shorting medium as it is retained in the packaging. This eliminates the labor associated with removing the spring from the sensor, or reduces the time required to match the electrodes with the instrument driver circuit or other shorting method for manufacturers who opt not to request a shorting spring.

In another aspect, a common shorting method is provided for sensors packaged individually or bulk packed. For example, for sensor manufacturers who store all sensors in bulk trays prior to shipping and then configure packing to suit orders, the conductive material (whilst retained by the tray) could be detached via an intentional break point to allow sensors to be individually removed from the storage trays with the conductive material still attached to the sensor—allowing the sensor to be packaged individually without re-introducing a manual springing operation.

An exemplary conductive material would preferably exhibit electrical characteristics of <10 KOhms between the sensor contacts and have elastic properties sufficient to maintain contact resistance over shelf storage life. A conductive foam in accordance herewith can be shaped and incorporated into a carrier tray. The foam can be configured to provide a short between only the sensor contacts which require shorting to one another. Other contacts are isolated.

In designing the properties of the shorting foam, or, link, it is useful to recognize how such sensors are shorted within unpowered instruments. This is useful to avoid the same type of start-up problems as can occur on first integration of a new sensor into the instrument. A recommended shorting resistor has a value on the order of 10K ohms.

In yet another embodiment, a bulk packaging tray can be designed to retain the foam so that when a sensor is removed from a tray it is asynchronously unshorted. The foam can be designed to be used to pack sensors in bulk trays. Alternately, the foam can be interrupted to provide a shorting method for individual sensors.

With respect to the figures, a packaging unit 10 includes a tray 12 which could be molded plastic or formed of a degradable, cardboard-like material. The tray 12 is substantially rigid and can be formed in a variety of shapes without limitation. The form factor of the tray 12 is not a limitation hereof.

The tray 12 includes or defines a plurality 14 of cavities or pockets which receive and carry sensors, or other electronic components. The exact shape of the pockets 14 is not a limitation, except as described subsequently.

As illustrated the pockets 14a, 14b can be formed or molded to any convenient shape for the component to be received in the packaging 10. Where large numbers of components are to be packaged the members of the plurality 14 can be substantially identical.

A plurality of conductive foam inserts 18 is carried by the tray 12. Members of the plurality 18, such as insert 18a, as described above are loaded with carbon to form a shorting resistive element which interacts with selected electrodes, or pins, of sensors 20, 20a or other components to be carried by packaging 10.

Figure 2:
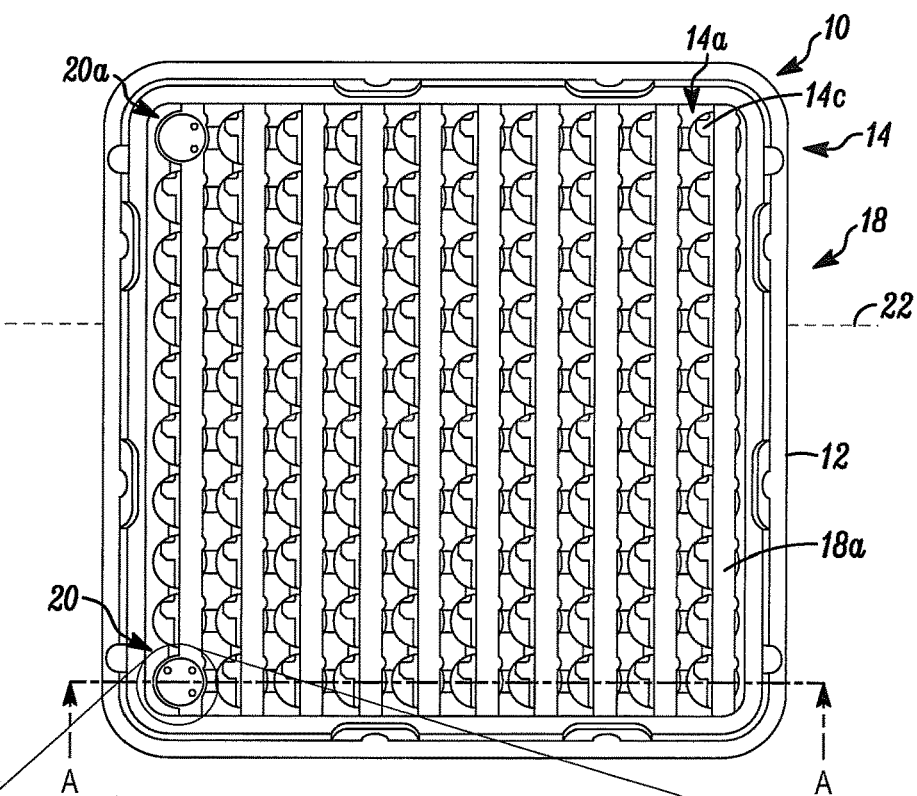
FIG. 2 is a plan view of the system of FIG. 1.
Figure 3:
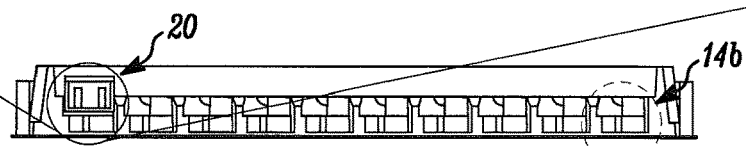
FIG. 3 is a sectional view taken along plane A-A of FIG. 2.
Figure 4:
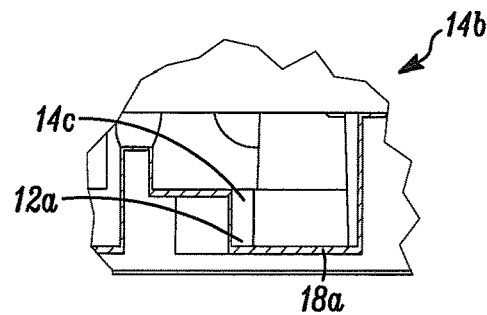
FIG. 4 is an enlarged view of a portion of the sectional view of FIG. 3.

In FIG. 2, the sensors 20, 20a are illustrated with their covers removed to illustrate how selected pins or electrodes can extend to and be in contact with the adjacent portion of insert, such as 18a, to implement the shorting function between those pins. As shown in FIG. 4, the respective cavity 14b can include an open region, illustrated by recessed surface 14c into which a non-shorted pin is to extend, adjacent to but displaced from the respective portion of insert 18a.

As best seen in FIG. 4, with respect to representative cavity 14b, tray 12 can be formed with a trough 12a which extends through a plurality of the cavities 14b. The members of the plurality 18, such as 18a are slidably received in the trough 12a with a press fit. It will be understood that other attachment mechanisms, such as adhesive, or overhanging moldings can be used to retain the inserts in respective ones of the troughs such as 12a.

To provide flexibility, break away regions 22 can be provided for the inserts 18 and/or the tray 12. If desired, individual cavities, such as 14b can also be formed with bread away regions.

In summary, the shorting foam and tray are designed to selectively short only selected pins or electrodes. Other pins are left isolated, see FIG. 2.

The conductive foam is heavily carbon loaded to provide a resistance between pins of less than 10K ohms. When the sensor is inserted the pins slidably engage the adjacent conductive foam insert, see FIG. 4.

As the foam is cut into strips and held in position in the tray, only the selected pins are shorted. This selective shorting of only 2 pins on a 3 pin sensor, for example, or two pins of a two pin component is achieved using low cost foam, integrated in to the package. This results in cost and labor savings for the manufacturer of cells and instruments. Neither the total number of pins nor the shorted number, per component, are limitations hereof.

From the foregoing, it will be observed that numerous variations and modifications may be effected without departing from the spirit and scope hereof. It is to be understood that no limitation with respect to the specific apparatus illustrated herein is intended or should be inferred. It is, of course, intended to cover by the appended claims all such modifications as fall within the scope of the claims.

Further, logic flows depicted in the figures do not require the particular order shown, or sequential order, to achieve desirable results. Other steps may be provided, or steps may be eliminated, from the described flows, and other components may be add to, or removed from the described embodiments.

The invention claimed is:

1. An apparatus comprising:
   a multi-electrode electrochemical gas sensor comprising electrodes;
   a tray, wherein the tray comprises a plurality of moldable pockets each configured to removably hold the sensor, wherein each moldable pocket includes a recessed surface;
   a shorting element positioned on the tray, wherein the shorting element comprises a conductive foam;
   wherein the sensor is positioned and removably held within one of the moldable pockets of the tray;

wherein the multi-electrode electrochemical gas sensor is positioned in contact with the conductive foam;
wherein the shorting element is electrically connected to short selected electrodes to one another while the gas sensor is removably held in the tray, but wherein the selected electrodes are asynchronously unshorted upon removal of the gas sensor from the tray;
wherein the recessed surface is adjacent to the shorting element;
wherein the shorting element is sufficiently elongated to extend through the plurality of pockets; and
wherein the shorting element is received in an elongated depression formed in the tray which spans the plurality of pockets.

2. The apparatus of claim 1, wherein a pin is electrically coupled to a non-shorted electrode, and wherein the pin is positioned in an open region of the recessed surface.

3. The apparatus of claim 2, wherein portions of the tray include break-away segments whereby a portion carrying at least one cavity is separable from the remainder of the tray.

4. The apparatus of claim 1,
wherein the shorting element extends into at least one of the moldable pockets.

5. The apparatus of claim 4, wherein the tray defines a trough which receives the shorting element so as to provide a plurality of shorting regions in the tray.

6. The apparatus of claim 5, wherein the shorting element defines breakaway regions, whereby portions of the shorting element are separable from one another at predetermined regions.

7. The apparatus of claim 1, wherein the shorting element comprises carbon.

8. The apparatus of claim 1, wherein a resistance of the shorting element is less than 10,000 ohms.

9. The apparatus of claim 1, wherein the shorting element is retained in the tray.

10. The apparatus of claim 9, wherein at least some of the pockets comprise an electrode receiving recess.

11. An apparatus comprising:
a multi-electrode electrochemical gas sensor comprising electrodes;
a tray, wherein the tray comprises a plurality of moldable pockets each configured to removably hold the sensor, wherein each moldable pocket includes a recessed surface;
a shorting element positioned on the tray, wherein the shorting element comprises a conductive foam;
wherein the sensor is positioned and removably held within one of the moldable pockets of the tray;
wherein the multi-electrode electrochemical gas sensor is positioned in contact with the conductive foam;
wherein the shorting element is electrically connected to short selected electrodes to one another while the gas sensor is removably held in the tray, but wherein the selected electrodes are asynchronously unshorted upon removal of the gas sensor from the tray;
wherein the recessed surface is adjacent to the shorting element; and
wherein a pin is electrically coupled to a non-shorted electrode, and wherein the pin is positioned in an open region of the recessed surface.

12. The apparatus of claim 11, wherein the shorting element is sufficiently elongated to extend through the plurality of pockets.

13. The apparatus of claim 11, wherein portions of the tray include break-away segments whereby a portion carrying at least one cavity is separable from the remainder of the tray.

14. The apparatus of claim 11,
wherein the shorting element extends into at least one of the moldable pockets.

15. The apparatus of claim 14, wherein the tray defines a trough which receives the shorting element so as to provide a plurality of shorting regions in the tray.

16. The apparatus of claim 15, wherein the shorting element defines breakaway regions, whereby portions of the shorting element are separable from one another at predetermined regions.

17. The apparatus of claim 16, wherein the shorting element comprises carbon.

18. The apparatus of claim 11, wherein a resistance of the shorting element is less than 10,000 ohms.

19. The apparatus of claim 11, wherein the shorting element is retained in the tray.

20. The apparatus of claim 19, wherein at least some of the pockets comprise an electrode receiving recess.

* * * * *